United States Patent [19]

Kawahara et al.

[11] Patent Number: 4,842,517
[45] Date of Patent: Jun. 27, 1989

[54] ENDOSSEOUS IMPLANT HAVING MESH PORE STRUCTURE

[75] Inventors: Haruyuki Kawahara, Moriguchi; Katsumi Tanaka, Ninomiya; Yasuyuki Ashiura, Odawara; Motonobu Yoshimura, Samukawa, all of Japan

[73] Assignees: Haruyuki Kawahara, Osaka; Toho Titanium Co., Ltd., Tokyo, both of Japan

[21] Appl. No.: 103,433

[22] Filed: Sep. 30, 1987

[30] Foreign Application Priority Data

Dec. 5, 1986 [JP] Japan ................. 61-290126

[51] Int. Cl.$^4$ .................. A61C 13/00; A61C 8/00
[52] U.S. Cl. ................................ 433/173; 433/176; 623/16
[58] Field of Search ............ 433/172, 173–174, 433/175, 176; 623/18, 20, 22, 23, 16

[56] References Cited

U.S. PATENT DOCUMENTS

| 470,332 | 3/1892 | Friel | 433/175 |
|---|---|---|---|
| 2,835,033 | 5/1958 | Airosser | 433/173 |
| 3,465,441 | 9/1969 | Linkow | 433/176 |
| 3,906,550 | 9/1975 | Rostoker et al. | 623/18 X |
| 3,952,414 | 4/1976 | Shovers et al. | 433/173 |
| 3,979,828 | 9/1976 | Taylor | 433/175 |
| 4,038,703 | 8/1977 | Bokros | 623/18 X |
| 4,261,063 | 4/1981 | Blanquaert | 623/18 |
| 4,351,069 | 9/1982 | Ballintyn et al. | 433/176 X |
| 4,439,152 | 3/1984 | Small | 433/174 X |
| 4,479,271 | 10/1984 | Balesky et al. | 623/18 X |
| 4,495,664 | 1/1985 | Blanquaert | 623/23 |
| 4,576,271 | 2/1986 | Sump | 623/18 |
| 4,744,755 | 5/1988 | Ross | 433/173 |

FOREIGN PATENT DOCUMENTS

| 1042834 | 11/1958 | Fed. Rep. of Germany | 433/174 |
|---|---|---|---|
| 0581938 | 11/1977 | U.S.S.R. | 623/16 |
| 1203093 | 8/1970 | United Kingdom | 433/174 |

OTHER PUBLICATIONS

EP 0189546, Semlitsch, 8/1986, (623/18).

Primary Examiner—Robert E. Garrett
Assistant Examiner—Carl D. Pride
Attorney, Agent, or Firm—Koda and Androlia

[57] ABSTRACT

An endosseous implant having a mesh pore structure including at least an embedding portion to be embedded in a living bone tissue, the embedding portion being a single sheet of a platelike body or a desired shape of body obtained by working the platelike body. The platelike body can be a single metal mesh sheet or a laminate of a plurality of metal mesh sheets formed into one body by mechanical bonding or by sintering, the laminate having a multiplicity of mesh pores passing through the embedding portion, whereby the embedding portion provides a mesh pore structure adapted to permit into the mesh pores the ingrowth and penetration of a fibrous tissue along out of three kinds of bone, osteoid, and fibrous tissues or not less than two tissues inclusive of the fibrous tissue.

6 Claims, 4 Drawing Sheets

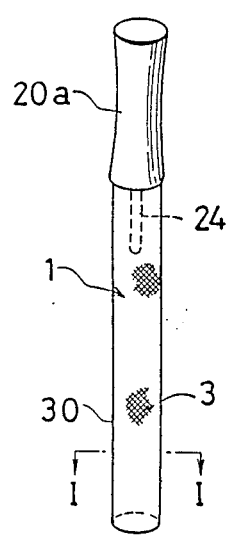
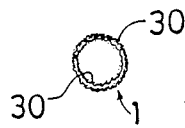
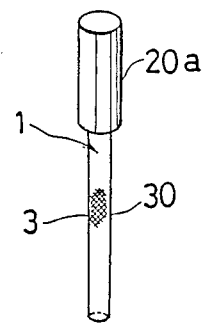
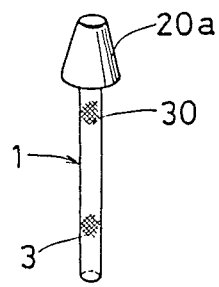
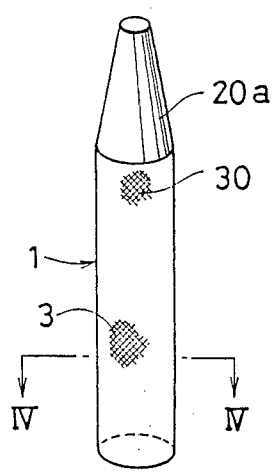
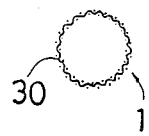

ENDOSSEOUS IMPLANT HAVING MESH PORE STRUCTURE

BACKGROUND OF THE INVENTION

1. Field of the Invention

This invention relates to an endosseous implant for prosthesis embedded in the bone tissue of a living body and more particularly to an endosseous implant for dental prosthesis or orthopedic surgery and having a mesh pore structure adapted for any implant used in the form of a platelike, tubular or columnar body.

2. Prior Art

Conventionally well known is a ceramic implant such as described in U.S. Pat. No. 4,259,072 in the form of a prosthetic member for a living body and such an implant as disclosed in Japanese Patent Laid Open Publication No. 10163/1982 wherein metal beads such as titanium, zirconium are sintered for use in an aritificial tooth root.

But in the former ceramic implant described above, the opening size of the pore, shape of netlike root, pore size and pore distribution in the ceramic implant, depend upon the kind of foaming agent making ceramics porous or upon sintering conditions so that it is difficult to artificially control the desired shape, size and distribution of the pores. On the other hand, since the latter implant has a core metal around which the above mentioned metal beads are sintered, is composed of composite bodies of core metal and metal grains sintered therearound, the implant necessarily has a limit on the minimal value of the diameter of a column. Supposing that the core metal is for example 2 mm in diameter and sintering materials are sintered therearound, the diameter of the column eventually measures at least more than 4 mm, with the result that the columnar sintered metal grain body can be used only in the alveolar bone having a large width and makes difficult its application to the case wherein the width of the alveolar bone is relatively small. The two types of implant mentioned above are not free from the problems described above.

Such being the case, the present inventors previously provided an implant (Japanese Patent Application No. 264994/1985) having a plurality of straight tubular cylindrical channels permitting the ingrowth and penetration of bone tissue, osteoid tissue and fibrous tissues into a metal plate as of titanium and zirconim, and also provided an implant of a platelike body of sintered metal beads and a frame integrally bound around the body, into which platelike body the ingrowth and penetration of the bone tissues is permitted. Each of the previous implants thus provided contributed greatly toward increased adaptability of the endosseous implant by enabling an architectural structure of bone made of both hard and soft tissues to hold the implant biodynamically in the interface between the implant and the bone tissue.

The inventors, after further research, have found that the former implant constructed by forming tubular cylindrical channels in the metal plate leaves a problem to be solved in making pores of various diameters and that the latter implant produced by sintering the beads into a plate form also not only makes it comparatively cumbersome in its manufacturing step to form desired pores with desired geographical distribution but also needs additional beads for making up for fissured clearance produced between a frame and the beads by contraction of the metal beads after the beads have been sintered. The implants thus have the problems yet to be solved.

SUMMARY OF THE INVENTION

Accordingly, the invention has for its object the provision of an endosseous implant having a mesh pore structure which is artificially placed in a living bone tissue. Various kinds of commercially available wire mesh made of a titanium-, or zirconium-, tantalum-based metal material are able to be use to build the mesh pore structure in the implant and the mesh can be worked into various shapes and sizes by a simple method of production, namely can be arranged so as to have various pore diameters.

BRIEF DESCRIPTION OF THE DRAWINGS

FIGS. 1 through 13 are embodiments of the invention, more particularly,

FIG. 1 (A) is a perspective view of a cylindrical implant and showing an embodiment of a multilayer mesh structure with no reinforcing frame;

FIG. 1 (B) is a sectional view taken along the line I—I in FIG. 1;

FIGS. 2 and 3 are perspective views showing substantially the same mesh structure as FIG. 1 except for, a different post shape;

FIG. 4 (A) is a perspective view of an embodiment of a single layer mesh structure having no reinforcing frame;

FIG. 4 (B) is a sectional view taken along the line IV—IV in FIG. 4 (A);

FIG. 5 is a perspective view of an embodiment of an implant having a reinforcing core formed in the lower part of a post;

FIG. 6 is a longitudinal sectional view showing another construction of an implant having a reinforcing core formed likewise in the lower part of the post;

FIG. 7 is a perspective view of another embodiment of the implant having likewise a reinforcing frame formed in the lower part of the post;

FIG. 8 is a sectional view taken along the line VIII—VIII in FIG. 7;

FIG. 9 is a perspective view showing another embodiment of the implant having likewise a mesh frame likewise directly below the post;

FIGS. 10 to 12 are perspective view showing embodiments of platelike implants having reinforcing frames used therein, respectively; and FIG. 13 is a perspective view showing another structure of the platelike implant having likewise a platelike reinforcing frame used therein.

DETAILED DESCRIPTION OF THE INVENTION

Figure 5:
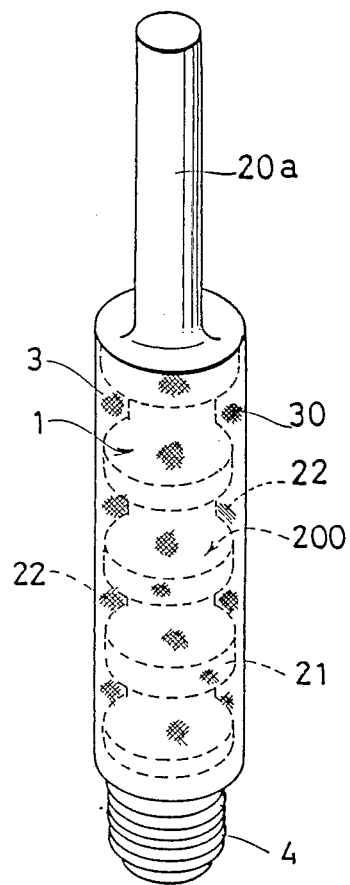

As shown in FIGS. 1 to 13 illustrating the embodiments thereof, the invention relates to an endosseous implant having a mesh pore structure and having at least an embedding portion to be embedded in a living bone tissue. The embedding portion includes either a sheet of platelike body or a body worked from the platelike body into a desired shape. The platelike body is formed of a single metal mesh sheet or a laminate of a plurality of metal mesh sheets formed by being mechanically bonded or sintered into one body and having a plurality of mesh pores passing through the thickness of the embedding portion, whereby the implant is enabled to have such a mesh pore structure as permits into the mesh pores the ingrowth and penetration of a fibrous tissue alone out of three kinds of bone, osteoid, and fibrous tissues or not less than two tissues inclusive of the fibrous tissue.

In the invention, the above mentioned metal mesh sheet is inclusive of not only a single kind of metal mesh sheet but also an alloy mesh sheet.

The invention can be practised in two cases. One is the case wherein an embedding portion 1 is used by being reinforced with a reinforcing core 200 or a reinforcing frame 2, 20. The other is the case wherein no such reinforcement is necessary. Namely, when the strength of the embedding portion 1 is compatible with the cause of the disease the use of such a reinforcing member is not necessary, and when incompatible, the reinforcing core 200 or the reinforcing frame 2, 20 is used. The pores 3 of the embedding portion 1 are formed by the use of a single layer mesh sheet or by the use of a plurality of mesh sheets laid one over another with their meshes concentrically aligned in the direction of the thickness of the bodies. When a plurality of mesh sheet is used in plural, various means of lamination may be contrived, for example, in such a manner that a metal mesh sheet small in mesh pore diameter is laid over another mesh sheet large in mesh pore diameter or sheets the same in mesh pore diameter are laid one over another in staggered relation with one another.

Different kinds of pores 3 formed in the embedding portion 1 range from approximately 30 to 1000 $\mu m$ in mean pore diameter and can be classified such that the pore diameter for the ingrowth and penetration of a bone tissue is not less than 100 $\mu m$, that for the ingrowth and penetration of an osteoid tissue is 40 to 100 $\mu m$, and that for the ingrowth and penetration of a fibrous tissue is not more than 40 $\mu m$.

The range in which the above ranges of pore diameter in the laminate overlap one another does not indicate a range of numerical value set for limiting the ingrowth and penetration of each tissue to any one of the above tissues but indicates that plural living tissues can mixedly make ingrowth and penetration into the laminate.

In this manner, the range of pores 3 in the invention and the geographical distribution of pores 3 can be established artificially and freely by suitably selecting a metal mesh sheet and/or alloy mesh sheet 30 with different mesh pore diameters and distributing the mesh sheets with such different pore diameters.

Even when the main portion 1 is reinforced with the reinforcing core 200 or reinforcing frame 2, 20, the main portion 1 of the mesh sheet is so made as to permit a fibrous tissue alone out of the bone, osteoid, and fibrous tissues or not less than two kinds of tissue inclusive of at least the fibrous tissue to pass through the thickness of the mesh sheet via the pores 3 from inside and outside of the embedding portion.

The endosseous implant makes it possible to build an architectural structure of bone between the implant and the living tissue by the ingrowth and penetration of a fibrous tissue with low elastic modulus and high shock resistance or not less than two tissues inclusive of the fibrous tissue selected from the bone, osteoid and fibrous tissues respectively from inside and outside of the embedding portion into the pores 3 different in diameter which are formed in the direction of the thickness of the embedding portion 1. When the architectural structure has been formed, the structure brings the interface between the adjacent bone tissues on both sides of the thickness of the embedding portion 1 into biodynamic connection to be able to embody conditions of maintaining natural tooth root in the alveolar bone.

Now, a description will be given of the embodiments of the invention with reference to FIGS. 1 to 13.

As shown in FIGS. 1 (A) and (b), 2 and 3, the implant embodying the invention is an implant comprises a hollow embedding portion 1 and a cylindrical or frustoconical post 20a connected concentrically integral with the upper side of the portion 1 by mechanical bonding or by sintering, wherein the post 20a is designed to receive a prosthetic member (an artificial tooth or the like) thereon and wherein the portion 1 is formed of plural sheets of a plurality of metal mesh sheets and/or alloy mesh sheets 30 (metal mesh sheets alone referred to hereinafter as an example) which are laminated one over another into one body by mechanical bonding or by sintering and is curvedly formed into a longitudinally cylindrical shape.

The post 20a in FIG. 1 is provided in its lower part with a pin 24 to be inserted into a pin hole (not shown) formed in an alveolar bone (not shown) so as to improve the stability of the embedding portion 1 embedded in the alveolar bone.

FIG. 4 (A) shows an implant constructed, of a hollow embedded portion 1 formed by curving a platelike mesh body of a single substance of metal mesh sheet 30 into a longitudinally cylindrical shape in combination with a frustoconical post 20a connected integrally with the top side of the portion 1. FIG. 4 (B) is a sectional view taken along the line IV—IV in FIG. 4 (A).

The above mentioned multilayer embedding portion 1 is formed by suitably selecting and laminating metal mesh sheets 30, of the same or different in mesh pore diameter, a metal mesh sheet of a single material as of titanium, zirconium, tantalum less harmful to the living tissue and titanium-, zirconium-, or tantalum-based alloy, Fe—Ni—Cr alloy, Co—Cr—Mo alloy, and by mechanically bonding or sintering the mesh sheets 30 into one body in a vacuua, or in inert gas atmosphere.

The embedding portion 1 of a single mesh sheet is also formed of similar metal mesh or alloy mesh sheet.

FIG. 5 shows a case wherein the post 20a is provided in its lower part with a reinforcing core 200. The reinforcing core provided in the form of a longitudinally cylindrical body includes a plurality of horizontal flanges 21, 21 formed spacedly away from one another longitudinally of the core. The metal mesh sheets 30 are wound round the periphery of the core 200 to form an embedding portion 1, and the mesh sheets 30 and the core 200 are bonded into one body by being mechanically bonded or by being sintered in vacuo or in inert gas atmosphere.

FIG. 5 structure makes it possible for the thus wound metal mesh sheets 30 to be supported along the periphery of the core 200 and to prevent the cores from being circumferentially deformed by the presence of the flanges 21, 21. Furthermore, the structure makes it possible for a fibrous tissue alone or not less than two tissues including at least the fibrous tissue out of bone, osteoid and fibrous tissues to make ingrowth and penetration from the spaces 22, 22 between the flanges into the core 200.

In FIG. 5, the numeral 4 indicates a tap to be screwed into a bone tissue when the core 200 is embedded in the bone tissue.

When the horizontal flange 21 of the reinforcing core 200 in FIG. 5, for example, is 3.5 $\phi$mm, the peripheral thickness of the embedding portion 1 is 0.75 mm in the spaces 22, 22 between the flanges 21, 21, and the sintered body forming the embedding portion 1 ranges in mesh diameter from 30 to 1000 μm as a standard.

Figure 6:
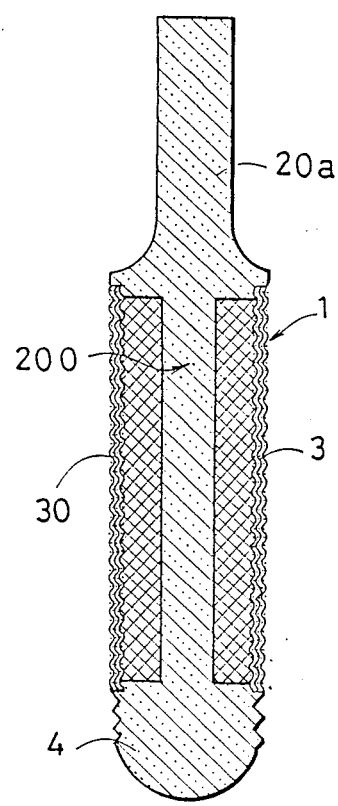
Figure 8:
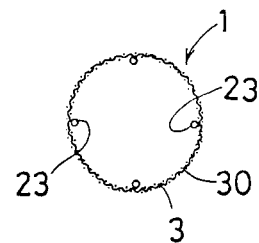
Figure 7:
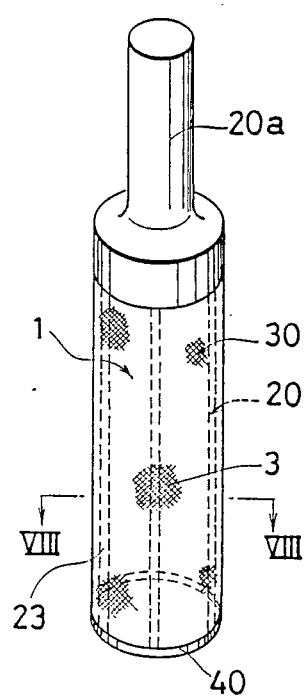

An embodiment shown in FIG. 6 (Sectional view) is the case wherein the implant is formed of a peripherally reduced reinforcing core 200 provided below the post 20a, a tap 4 substantially the same in diameter with the post 20a, and metal mesh sheets 30 wound around the outer periphery of the reinforcing core 200. FIG. 7 shows another embodiment of the invention wherein the post 20a is provided in its lower part with a reinforcing frame 20. The reinforcing frame 20 includes plural rods 23, 23 extending vertically downwardly from the underside of the post 20a with suitable intervals provided circumferentially between the rods with their lower ends fixed to a ringlike frame 40 and with the metal mesh sheets 30 wound peripherally of the frame 20 to thereby form the embedding portion 1. FIG. 8 is a sectional view taken along the line VIII—VIII in FIG. 7.

Figure 9:
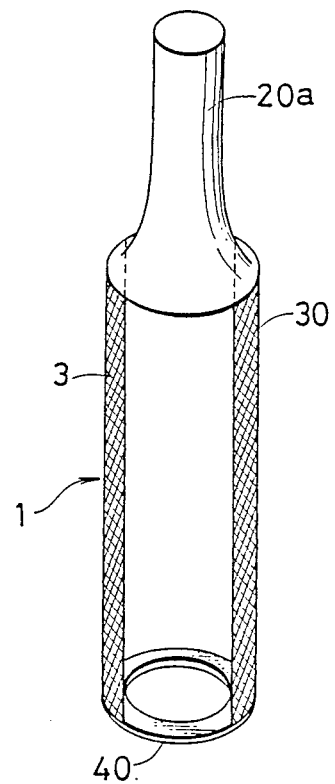

FIG. 9 shows another embodiment wherein the post 20a includes laminated metal mesh sheets 30 circularly disposed in the lower part of the post 20a, a ringlike frame 40 is secured to the lower side of the mesh sheets 30 to fix the mesh sheets 30.

Figure 10:
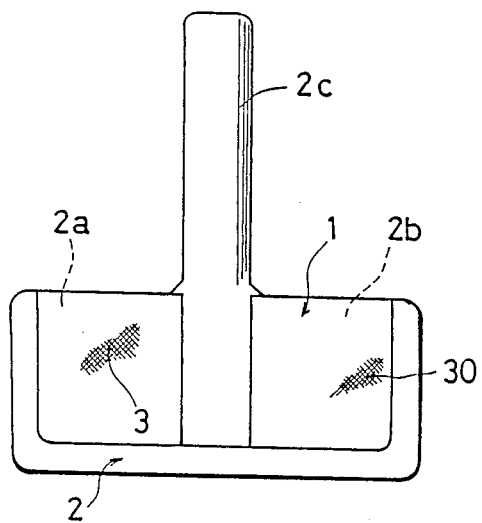

FIG. 10 shows another embodiment showing another structure of the dental endosseous implant of the invention, which comprises an inverted T-shaped reinforcement frame 2 and a platelike embedding portion 1 comprising a plurality of metal mesh sheets 30 integrally and fixedly supported in U-shaped right and left openings 2a, 2b of the frame 2 by sintering.

Figure 11:
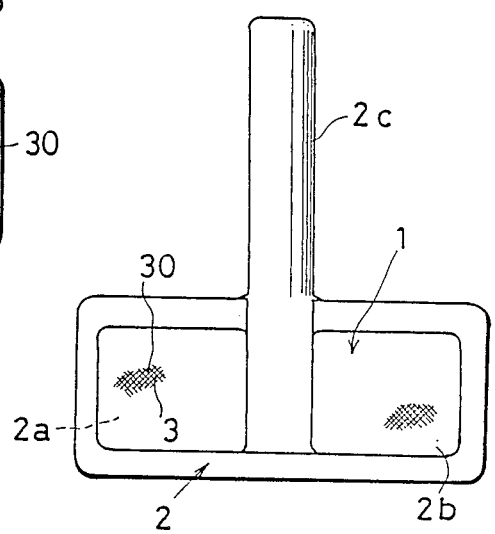
Figure 12:
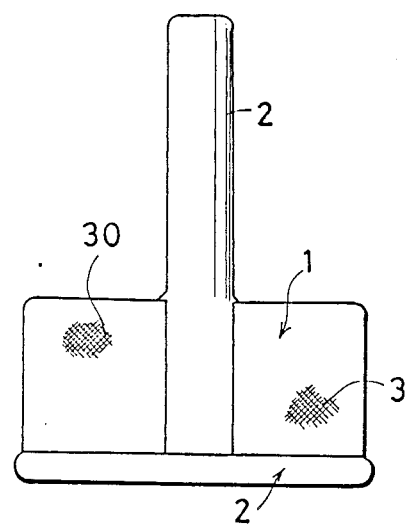

Namely, the platelike embedding portion 1 is formed by suitably selecting a single substance metal such as the aforementioned titanium, zirconium and tantalum less harmful to the living tissue, and alloy mesh sheets 30 as of titanium-, zirconium-, tantalum-based alloy, Fe—Ni—Cr alloy, Co—Cr—Mo alloy, making frame member 2 of a frame material same or compatible in property with the embedding portions 1 and 1, filling the U-shaped openings 2a and 2b with the metal mesh sheets 30 and sintering the mesh sheets integrally with the embedding portions 1 and 1 in vacuo or in inert gas atmosphere. As a result, the embedding portions 1 and 1 are fixedly supported in a platelike area of the reinforcing frame 2 as a multilayer sintered body which permits the ingrowth and penetration of a fibrous tissue alone or not less than two kinds of tissue containing at least the fibrous tissue out of bone, osteoid, and fibrous tissues into the sintered multilaminate body. FIGS. 11 and 12 show an embodiment (FIG. 11) having a reinforcing frame 2 having the openings 2a and 2b enclosed with a frame formed by extending the E-shaped frame in FIG. 10 and an embodiment (FIG. 12) wherein the frame 2 is brought into an inverted T-shape and has L-shaped openings on the right and left thereof, respectively.

For example, when the reinforcing frames 2 in FIGS. 10 to 12 are comprised of titanium, or zirconium or its alloy, or tantalum, tantalum alloy, Fe—Ni alloy, Co—Cr—Mo alloy or the like, the thickness of the platelike embedding portion 1 is 2.5 mm maximally and the mesh of the sintered boy constituting the portion 1 is in the range of 150 to 500 μm on the average as a standard.

Figure 13:
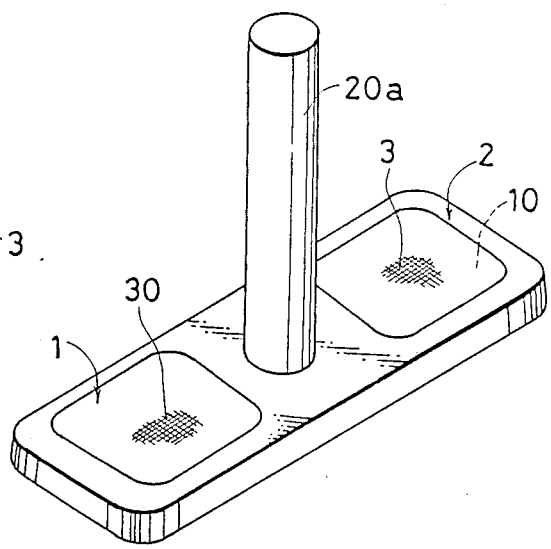

On the other hand, the shape of the reinforcing frame 2 is determined suitably in accordance with the external force applied to the implant in time of treatment and with the thickness of the embedding portion 1. FIG. 13 shows still another embodiment, wherein the reinforcing frame 2 comprises a sheet of platelike body having through holes 10 and 10 on the right and left thereof, and a platelike embedding portions 1 and 1 respectively formed of sintered body having the metal mesh sheets 30 therein are fixed integrally with the frame 2 within the through holes 1 and 1.

When the reinforcing frame 2 formed of the platelike body is made of titanium or zirconium or its alloy or tantalum, tantalum alloy, Fe—Ni alloy, Co—Cr—Mo alloy or the like, through holes, 10, 10 are, for example 10 mm in diameter respectively, and the thickness of the hole within which the above sintered body is fixed integrally with the frame 2 to form the embedding portion, 1 is 2.5 mm at maximum.

In accordance with the clinical cause of the disease, it is suitably adopted that for example, a post 20a in FIG. 13 is set in about the center of the reinforcing frame 2 and an artificial bone or the like is mounted on the top of the post 20a. The foregoing description has been given of the invention with reference to the use of metal (or alloy) mesh sheet but application of ceramic mesh or plastic mesh material unharmful to a living body is not objectionable.

As described above, the endosseous implant having a mesh pore structure according to the invention has, in addition to the advantage disclosed in our previous patent application, the advantage that, by the anchoring effect provided by the ingrowth and penetration of a living tissue into a plurality of pores formed in an embedding portion, a platelike embedding portion after the ingrowth and penetration makes biodynamic connection with the bone tissue adjacent thereto to thereby obtain an artitectural structure of bone on both sides of the embedding portion, and is also superior to conventional implants in the ease of working, namely, in that the implant can form, by the use of readily available mesh sheet, an embedding portion worked into a plate form or a desired form having various pores which permit the ingrowth and penetration thereinto of a fibrous tissue alone or not less than two kinds of tissue inclusive of at least the fibrous tissue out of bone, osteoid, and fibrous tissues and in addition, can build an architectural structure of bone by piercing through the width of the embedding portion and permit the ingrowth and penetration of living bone tissue from inside and outside of the embedding portion thereinto. If necessary, the implant of the invention can provide the advantage that an implant having a mesh structure can be obtained by its more sintering integrally with a post or a reinforcing core or a reinforcing frame so that the easy workability of the implant, in turn, can reduce production cost.

I claim:

1. An endosseous implant having a mesh pore structure comprising a portion to be embedded in a living bone tissue, said embedding portion comprising a hollow cylindrical body having two surfaces and being formed from at least a single sheet of metal mesh and into a desired shape by working the single sheet of metal mesh, said embedding portion having a multiplicity of mesh pores passing therethrough, whereby the embedding portion provides a mesh pore structure for ingrowth and penetration of said living bone tissue into both surfaces of said embedding portion;

a post for mounting a prosthetic member thereon connected to said embedding portion; and a reinforcing frame for reinforcing the embedding portion connected to said post, whereby said hollow cylindrical body is reinforced to prevent circumferential deformation and said reinforcing frame includes a plurality of vertical rods provided spacedly away from one another along a peripheral direction of said post and has a ring-like frame secure to ends of said rods.

2. An endosseous implant having a mesh pore structure comprising a portion to be embedded in a living bone tissue, said embedding portion comprising two plate-like members having two surfaces and being formed from at least a single sheet of metal mesh and into a desired shape by working the single sheet of metal mesh, said embedding portion having a multiplicity of mesh pores passing therethrough, whereby the embedding portion provides a mesh pore structure for ingrowth and penetration of said living bone tissue into both surfaces of said embedding portion;
 a post for mounting a prosthetic member thereon connected to said embedding portion; and
 a reinforcing frame for reinforcing the embedding portion connected to said post, said two plate-like members extending laterally from said post, said plate-like members being held and fixed by said reinforcing frame.

3. An endosseous implant according to claim 2 wherein said reinforcing frame is an E-shaped reinforcing frame and said platelike members are held and fixed in U-shaped openings on opposing sides of said reinforcing frame.

4. An endosseous implant according to claim 3 wherein the open sides of said E-shaped reinforcing frame are closed by an extended frame.

5. An endosseous implant according to claim 2 wherein said reinforcing frame is inverted T-shaped and said plate-like members are held and between the perpendicular legs of both sides of said T-shaped frame.

6. An endosseous implant according to claim 2 wherein said reinforcing frame comprises a sheet-like body attached at its center to said post, and having through holes formed opposite sides of said post said plate-like members are held and fixed in said holes, respectively.

* * * * *